(12) United States Patent
Pinski

(10) Patent No.: US 8,354,126 B1
(45) Date of Patent: Jan. 15, 2013

(54) COMPOSITION FOR PROSTATE HEALTH

(75) Inventor: Jacek Pinski, La Canada Flintridge, CA (US)

(73) Assignee: OncoNatural Solutions, Inc., Los Angeles, CA (US)

( * ) Notice: Subject to any disclaimer, the term of this patent is extended or adjusted under 35 U.S.C. 154(b) by 0 days.

(21) Appl. No.: 13/179,981

(22) Filed: Jul. 11, 2011

Related U.S. Application Data

(62) Division of application No. 12/137,713, filed on Jun. 12, 2008, now Pat. No. 8,221,803.

(60) Provisional application No. 60/945,992, filed on Jun. 25, 2007.

(51) Int. Cl.
*A01N 59/06* (2006.01)
*A61K 33/06* (2006.01)

(52) U.S. Cl. ........................................................ 424/682

(58) Field of Classification Search .................. 424/682
See application file for complete search history.

(56) References Cited

U.S. PATENT DOCUMENTS

| | | |
|---|---|---|
| 5,543,146 A | 8/1996 | Perez |
| 5,795,882 A | 8/1998 | Bishop et al. |
| 5,830,887 A | 11/1998 | Kelly |
| 6,004,558 A | 12/1999 | Thurn et al. |
| 6,117,429 A | 9/2000 | Bucci |
| 6,197,309 B1 | 3/2001 | Wheeler |
| 6,241,987 B1 | 6/2001 | Lam |
| 6,261,565 B1 | 7/2001 | Empie et al. |
| 6,261,607 B1 | 7/2001 | Newmark et al. |
| 6,329,357 B1 | 12/2001 | Norman et al. |
| 6,350,776 B1 | 2/2002 | Azzi |
| 6,399,115 B2 | 6/2002 | Revel |
| 6,482,447 B2 | 11/2002 | Revel |
| 6,497,906 B1 | 12/2002 | Kelly |
| 6,509,381 B2 | 1/2003 | Empie et al. |
| 6,562,380 B1 | 5/2003 | Kelly |
| 6,652,890 B2 | 11/2003 | Moore et al. |
| 6,656,509 B1 | 12/2003 | Stiefel et al. |
| 6,670,392 B2 | 12/2003 | Fleshner |
| 6,713,506 B2 | 3/2004 | Dou et al. |
| 6,733,796 B2 | 5/2004 | Randhava et al. |
| 6,821,532 B2 | 11/2004 | Randhava et al. |
| 6,900,240 B2 | 5/2005 | Empie et al. |
| 7,022,350 B2 | 4/2006 | Harvey et al. |
| 7,067,159 B2 | 6/2006 | Newmark et al. |
| 7,070,816 B2 | 7/2006 | Newmark et al. |
| 7,285,279 B2 | 10/2007 | Sun |
| 7,396,855 B2 | 7/2008 | Setchell et al. |
| 7,405,227 B2 | 7/2008 | Kun et al. |
| 7,445,807 B2 | 11/2008 | Lockwood |
| 7,470,440 B2 | 12/2008 | Newmark et al. |
| 7,597,910 B2 | 10/2009 | McDowell, Jr. |
| 7,629,005 B2 | 12/2009 | Popp |
| 7,670,612 B2 | 3/2010 | Miller |
| 2001/0028897 A1 | 10/2001 | Hammerly |
| 2001/0031744 A1* | 10/2001 | Kosbab ............................ 514/54 |
| 2002/0127243 A1 | 9/2002 | Sun |
| 2002/0137731 A1 | 9/2002 | Gewirtz |
| 2002/0169195 A1 | 11/2002 | Kindness et al. |
| 2002/0176898 A1 | 11/2002 | Morre et al. |
| 2003/0018060 A1 | 1/2003 | Kelly et al. |
| 2003/0064938 A1 | 4/2003 | Empie et al. |
| 2003/0236301 A1 | 12/2003 | Sanders et al. |
| 2004/0023925 A1 | 2/2004 | Chang et al. |
| 2004/0247619 A1 | 12/2004 | Hambrook |
| 2004/0248971 A1 | 12/2004 | Yeh et al. |
| 2004/0258757 A1 | 12/2004 | Bosch et al. |
| 2004/0259815 A1 | 12/2004 | Van Helvoort et al. |
| 2004/0259816 A1 | 12/2004 | Pandol et al. |
| 2005/0002992 A1 | 1/2005 | McCleary et al. |
| 2005/0026852 A1 | 2/2005 | Rustum et al. |
| 2005/0032882 A1 | 2/2005 | Chen |
| 2005/0191368 A1* | 9/2005 | Harvey et al. ............ 424/641 |
| 2005/0208070 A1 | 9/2005 | Dao et al. |
| 2005/0220908 A1 | 10/2005 | Theoharides |
| 2005/0220909 A1 | 10/2005 | Theoharides |
| 2005/0220912 A1 | 10/2005 | Theoharides |
| 2005/0220949 A1 | 10/2005 | Arzubi |
| 2005/0260285 A1 | 11/2005 | DiMateeo-Leggio |
| 2006/0009430 A1 | 1/2006 | Kelly |
| 2006/0020046 A1 | 1/2006 | Goralczyk et al. |
| 2006/0069151 A1 | 3/2006 | Barella et al. |
| 2006/0104901 A1 | 5/2006 | Moodycliffe et al. |
| 2006/0121129 A1 | 6/2006 | Harvey et al. |
| 2006/0233809 A1 | 10/2006 | Smith et al. |
| 2006/0246153 A1 | 11/2006 | Bombardelli et al. |
| 2006/0258697 A1 | 11/2006 | Rustum et al. |
| 2006/0275294 A1 | 12/2006 | Omoigui |
| 2006/0276372 A1 | 12/2006 | Lockwood et al. |
| 2007/0037879 A1 | 2/2007 | Wechter |
| 2007/0048296 A1 | 3/2007 | Kajander et al. |

FOREIGN PATENT DOCUMENTS

| | | |
|---|---|---|
| DE | 4442766 | 6/1996 |
| DE | 10026937 | 12/2001 |

(Continued)

OTHER PUBLICATIONS

Oh et al. (Activity of the herbal combination, PC-SPES, in the treatment of patients with androgen-independent prostate cancer, Urology 57: 122-126, Elsevier Science 2001).*

*Primary Examiner* — Fereydoun G Sajjadi
*Assistant Examiner* — Danielle Sullivan
(74) *Attorney, Agent, or Firm* — Amin Talati, LLC; Janine A. Moderson

(57) ABSTRACT

The present invention provides an effective, all-natural, non-toxic, non-hormonal composition consisting of vitamin D3, vitamin E, selenium, green tea extract, saw palmetto berry extract, isoflavanoids, and lycopene for prostate health. The invention provides compositions and methods to prevent, alleviate, and/or treat symptoms associated with prostate conditions and diseases. The prostate health composition may be used to supplement medical treatment such as radiation therapy, chemotherapy, and hormone therapy.

20 Claims, No Drawings

FOREIGN PATENT DOCUMENTS

| | | |
|---|---|---|
| EP | 0600544 | 6/1994 |
| FR | 2770975 | 5/1999 |
| FR | 2806263 | 9/2001 |
| JP | 06227970 | 8/1994 |
| JP | 10127249 | 5/1998 |
| JP | 10158182 | 6/1998 |
| WO | 9833494 | 8/1998 |
| WO | 9848790 | 11/1998 |
| WO | 9911279 | 3/1999 |
| WO | 2005027923 | 3/2005 |

* cited by examiner

COMPOSITION FOR PROSTATE HEALTH

This application claims the benefit of earlier filed U.S. patent application Ser. No. 12/137,713 filed on Jun. 12, 2008 which claims priority to the earlier filed U.S. Provisional Patent Application Ser. No. 60/945,992 entitled, "Composition for Prostate Health," filed on Jun. 25, 2007.

FIELD OF THE INVENTION

The present invention relates to a prostate health composition for treating, preventing, and/or alleviating the symptoms associated with prostate cancer, benign prostatic hyperplasia ("BPH"), and other prostate diseases, and prolonging prostate health. The present invention also relates to a method for treating, preventing, and/or alleviating the symptoms associated with prostate diseases utilizing a prostate health composition.

BACKGROUND OF THE INVENTION

Serious prostate diseases are experienced by one in six men over the age of 40, including prostate cancer. Additionally, BPH, a condition wherein the prostate is enlarged causing discomfort, frequent urination, and urgency of urination, is developed by more than half of all men over age 60. Prostate disease, especially prostate cancer, can be detected by higher than normal prostate specific antigen (PSA) levels. Normal PSA levels are defined as less than about 4 nanograms per milliliter (ng/mL). PSA is a protein produced by the prostate gland and is normally present in small amounts in men. However, with the presence of prostate disease, the level of PSA can be elevated beyond or above normal levels.

Treatments for prostate associated diseases include medications, surgery, chemotherapy, and/or radiation therapy. Often these treatments can prolong life, but can cause significant toxicities, reduction of enjoyment of life, significant side effects, a decrease in the immune system activity, and may not be curative.

A large retrospective analysis of men with PSA-only recurrence of prostate cancer after radical prostatectomy found that a Gleason Grade of 7 or higher and a PSA doubling time of 12 months or less defined a population of men for whom early androgen deprivation therapy (ADT) was associated with delayed development of clinical metastasis. For those at lower risk, in the absence of documented benefit for early ADT, a non-toxic, non-hormonal intervention would be preferable. Accordingly, there is a demand for a natural prostate health composition which is effective and less toxic than androgen ablation therapy, chemotherapy, and/or radiation therapy.

SUMMARY OF THE INVENTION

A general object of the present invention is to provide a prostate health composition which is all natural.

A more specific object of the present invention is to overcome one or more of the problems discussed above.

Another object of the present invention is to provide a prostate health composition which is more effective due to the synergistic effects of the combined ingredients.

A further object of the present invention is to provide a prostate health composition which is less toxic than androgen deprivation therapy, chemotherapy, or radiation therapy.

An even further object of the present invention is to provide a prostate health composition which supplements chemotherapeutic agents and/or radiation therapy.

A still even further object of the present invention is to treat prostate cancer such as by inhibiting increases in PSA levels and/or by reducing elevated PSA levels to a level which falls within a generally accepted normal range.

A yet even further object of the present invention is to treat prostate cancer such as by reducing the number of tumor cells present in the blood.

Another object of the present invention is to treat prostate cancer such as by inhibiting or reducing the growth and proliferation of prostate cancer cells and/or causing cell death to prostate cancer cells.

The prior art generally fails to provide a prostate health composition that is natural, safe, less toxic than hormonal, chemical, and/or radiation-based therapies, and as effective as may be desired. The prior art also generally fails to provide a prostate health composition wherein the ingredients work synergistically in combination to treat, prevent and/or, alleviate the symptoms associated with prostate cancer, benign prostatic hyperplasia ("BPH"), and other prostate diseases.

Accordingly, the prostate health composition has been developed to be all natural, less toxic than chemical and/or radiation-based therapies, and highly effective due to the synergistic effects of the combined ingredients. The general object of the present invention can be achieved, at least in part, through a prostate health composition containing vitamins, antioxidants, minerals, polyphenols, plant extracts, isoflavanoids, carotenoids, and combinations thereof.

In one embodiment of the present invention, the prostate health composition includes and/or consists of vitamin D3, vitamin E, selenium, green tea extract, saw palmetto berry extract, isoflavanoids, lycopene, and/or combinations thereof.

In another embodiment of the present invention, the prostate health composition includes and/or consists of cholecalciferol, d-alpha tocopherol, 1-selenomethionine, epigallocatechin, saw palmetto berry extract, daidzein, genistein, glycitein, lycopene, and/or combinations thereof.

The present invention also relates to a method for treating, preventing, and/or alleviating the symptoms associated with prostate diseases utilizing a prostate health composition.

These and other embodiments of the present invention are more fully described in connection with the detailed description.

DETAILED DESCRIPTION OF THE INVENTION

Generally prostate diseases, such as prostate cancer and benign prostate hyperplasia ("BPH"), are treated with drugs, such as hormonal therapy, chemotherapy, and/or radiation therapy, alone or in combination with surgical intervention such as, for example, a radical prostatectomy. These treatments are generally toxic, have significant side effects, and may not provide a cure while merely prolonging life. Accordingly, a prostate health composition has been developed which is designed to be natural, safe, less toxic than other chemical and/or radiation-based therapies, and highly effective wherein the ingredients work synergistically to treat, prevent, and/or alleviate the symptoms associated with prostate diseases and conditions.

In accordance with the present invention, a natural, effective prostate health composition, wherein the ingredients work synergistically together, has been developed. The prostate health composition of one form of the present invention treats, prevents, and/or alleviates symptoms associated with prostate diseases conditions, including prostate cancer and BPH. The general object of the present invention can be achieved, at least in part, through a prostate health composition containing vitamins, antioxidants, minerals, polyphenols, plant extracts, isoflavanoids, carotenoids, and combinations thereof.

In one embodiment of the present invention, the prostate health composition includes and/or consists of vitamin D3, vitamin E, selenium, green tea extract, saw palmetto berry extract, isoflavanoids, lycopene, and combinations thereof.

The individual ingredients of the present invention have generally been shown or are believed to individually have either a preventive or a therapeutic benefit when used to treat and/or alleviate the symptoms of prostate diseases and/or conditions. Vitamins D and E are antioxidants which are believed to lower the overall risk of prostate cancer. Selenium is believed to reduce the risk of prostate cancer, inhibit cell growth, and increase prostate cancer cell sensitivity to gamma-irradiation. Green tea extract is believed to contain tumor growth, kill prostate cancer cells, target prostate cancer cells without damaging benign cells, reduce the overall risk of prostate cancer, and enhance chemotherapeutic agents. Saw palmetto extract is believed to relieve the symptoms of BPH. Isoflavanoids are believed to reduce inflammation of the prostate associated with BPH, reduce growth of prostate cancer cells, inhibit prostate cancer cell proliferation, delay prostate specific antigen ("PSA") progression, and improve the therapeutic benefits of radiation therapy. Lycopene is an antioxidant believed to reduce the effect of testosterone on prostate cancer, reduce the overall risk of prostate cancer, inhibit prostate cancer cell proliferation, and increase the number of prostate cancer cells that undergo apoptosis.

In the present invention, combination therapy is undertaken with the goal of synergy, or at least additive effects with an improved side effect profile due to lower doses of each individual component. Given that the above-described agents or ingredients work diversely, with mechanisms of action varying from inhibition of cell cycling to induction of differentiation or apoptosis, it is believed that synergism is likely.

The vitamin D3, vitamin E, selenium, green tea extract, saw palmetto berry extract, isoflavanoids, lycopene, and/or combinations thereof of the present invention are believed to work in combination to synergistically treat, prevent, and/or alleviate symptoms associated with prostate diseases and conditions, including prostate cancer and BPH.

In another embodiment of the present invention, the prostate health composition includes and/or consists of cholecalciferol, d-alpha tocopherol, 1-selenomethionine, epigallocatechin, saw palmetto berry extract, daidzein, genistein, glycitein, lycopene, and/or combinations thereof.

In another embodiment of the present invention, the prostate health composition includes and/or consists of, in a daily dosage:
    about 200 IU to about 1200 IU of vitamin D3;
    about 200 IU to about 1200 IU of vitamin E;
    about 100 mcg to about 600 mcg of selenium;
    about 200 mg to about 1200 mg of epigallocatechin;
    about 160 mg to about 960 mg of saw palmetto berry extract;
    about 10 mg to about 60 mg of daidzein;
    about 10 mg to about 60 mg of genistein;
    about 10 mg to about 60 mg of glycitein; and
    about 5 mg to about 30 mg of lycopene.

In another embodiment of the present invention, the prostate health composition includes and/or consists of, in a daily dosage:
    at least about 200 IU of vitamin D3;
    at least about 200 IU of vitamin E;
    at least about 100 mcg of selenium;
    at least about 200 mg of epigallocatechin;
    at least about 160 mg of saw palmetto berry extract;
    at least about 10 mg of daidzein;
    at least about 10 mg of genistein;
    at least about 10 mg of glycitein; and
    at least about 5 mg of lycopene.

The following example of one embodiment of the present invention provides a prostate health composition, and demonstrates the scope of the present invention. The prostate health composition includes and/or consists of, in a daily dosage:
    about 400 IU of vitamin D3;
    about 400 IU of vitamin E;
    about 200 mcg of selenium;
    about 400 mg of epigallocatechin;
    about 320 mg of saw palmetto berry extract;
    about 20 mg of daidzein;
    about 20 mg of genistein;
    about 20 mg of glycitein; and
    about 10 mg of lycopene.

In another embodiment of the present invention, additional ingredients may include vitamin A, vitamin C, silica, magnesium, maltodextrin, and soy proteins.

In one embodiment of the present invention, the prostate health composition may be in a tablet, capsule, or soft gel dosage form. In another embodiment of the present invention, the prostate health composition may be a dietary supplement.

The present invention also relates to a method for treating, preventing and/or alleviating the symptoms associated with prostate diseases and conditions utilizing a prostate health composition which includes administering to a human the prostate health composition described above. In one embodiment of the present invention, the method includes administering to a human a daily dosage of the prostate health composition in about one to about eight capsules. The daily dosage can be administered in one administration, in two administrations, or in three administrations. The daily dosage can be administered with meals. The administering of the prostate health composition can be done for the duration of improvement of the underlying prostate condition. The prostate health composition can be administered with or without chemotherapy and/or radiation therapy.

In one embodiment of the present invention, the prostate health composition can be used to treat prostate cancer and/or lower PSA levels in patients having a recurrence of prostate cancer. Often patients having localized, non-metastatic prostate cancer undergo radiation therapy or surgery to remove the prostate as treatment of the prostate cancer. A recurrence of the prostate cancer can be found in these patients even after radiation therapy or removal of the prostate. The recurrence of the prostate cancer is identified by rising, elevated beyond or above normal, levels of PSA. This recurrence of prostate cancer may not be visible (i.e. no tumor formation). For example, in some cases, only biochemical markers, such as rising and/or elevated beyond or above normal levels of PSA indicate the presence of prostate cancer cells. A standard treatment does not exist for this group of patients. Hormone therapy and/or chemotherapy are treatments that are currently used. Hormone therapy blocks testosterone which the prostate cancer cells depend upon for proliferation and therefore can lower or reduce the elevated beyond or above normal levels of PSA. However, hormone therapy and chemotherapy are chemical treatments which must be injected or infused, may not produce uniform results, are toxic, and can cause hot flashes, weight gain, lethargy, depression, and sexual impotence, among other unwanted side effects. Accordingly, the ingredients of the present invention work synergistically in combination to orally treat recurrence of prostate cancer, inhibit or reduce the rate of elevation of PSA levels, and lower PSA levels. Additionally, the present invention is less toxic than chemical and/or radiation-based therapies, and does not have side effects.

In one embodiment of the present invention, the prostate health composition can be used to treat prostate cancer and inhibit or reduce the growth and proliferation of prostate cancer cells more effectively than the individual ingredients of the present invention alone. In another embodiment of the present invention, the prostate health composition can be used to cause prostate cancer cell death more effectively than the individual ingredients of the present invention alone.

In another embodiment of the present invention, the prostate health composition can be used to supplement radiation therapy and increase the apoptotic effect of radiation therapy on prostate cancer cells and provide more effective treatment of prostate cancer than the radiation therapy alone.

In another embodiment of the present invention, the prostate health composition can be used to treat and/or reduce the symptoms of BPH.

In another embodiment of the present invention, the prostate health composition can be used to treat prostate cancer and provide predictable results wherein the results for each patient would not be variable but standardized and predictable.

In another embodiment of the present invention, the prostate health composition can be used to target specific components of the cell proliferation cycle or alter regulation of the apoptotic pathways in the treatment of prostate cancer and can result in the increased death of prostate cancer cells.

While in the foregoing specification this invention has been described in relation to certain preferred embodiments thereof, and many details have been set forth for the purpose of illustration, it will be apparent to those skilled in the art that the invention is susceptible to additional embodiments and that certain details described herein can be varied considerably without departing from the basic principles of the invention.

The invention claimed is:

1. A method for improving prostate health, comprising:
  administering to a human a composition comprising in an effective daily dosage:
    at least about 200 International Units (IU) of cholecalciferol;
    at least about 200 IU of D-alpha tocopherol;
    at least about 100 micrograms (µg) of selenium as L-selenomethionine;
    at least about 200 milligrams (mg) of epigallocatechin;
    at least about 160 mg of saw palmetto berry extract;
    at least about 10 mg of daidzein;
    at least about 10 mg of genistein;
    at least about 10 mg of glycitein; and
    at least about 5 mg of lycopene,
    wherein the effective daily dosage of the composition reduces severity of at least one symptom associated with a prostate condition and/or disease, the symptom selected from the group consisting of frequent urination, urgency of urination, urinary hesitancy, weak urination, urinary blockage, urinary leakage, urinary dribbling, night urination, prostatitis, elevated prostate specific antigen levels, tumor cells, enlarged prostate, benign prostate hyperplasia, prostate cancer, and combinations thereof.

2. The method according to claim 1, wherein the effective daily dosage of the composition is administered in about 1 to about 8 individual doses for a period of time sufficient to provide improvement in the at least one symptom.

3. The method according to claim 1, wherein the composition is administered in an effective daily dosage to reduce a rate of prostate specific antigen (PSA) level elevation.

4. The method according to claim 1, wherein the composition is administered as an adjuvant to radiation therapy, chemotherapeutic agents, or a combination thereof.

5. The method according to claim 1, wherein the composition is administered in an effective daily dosage to alleviate at least one symptom associated with benign prostate hyperplasia.

6. The method according to claim 1, wherein the composition is administered in an effective daily dosage to reduce PSA levels in the human.

7. The method according to claim 1, wherein the composition is administered orally.

8. The method according to claim 1, wherein the composition is administered to a patient having a recurrence of prostate cancer in an effective daily dosage to lower elevated PSA levels.

9. The method according to claim 1, wherein the composition is administered to a patient having a recurrence of prostate cancer in an effective daily dosage to reduce proliferation of prostate cancer cells.

10. A method for reducing a rate of elevation of prostate serum antigen (PSA) in a patient having recurrence of prostate cancer, comprising:
  administering to the patient a composition comprising in an effective daily dosage at least about 200 International Units (IU) cholecalciferol, at least about 200 IU of D-alpha tocopherol, at least about 100 micrograms (µg) of selenium, at least about 200 milligrams (mg) of epigallocatechin, at least about 160 mg of saw palmetto berry extract, at least about 10 mg of at least one isoflavonoid compound selected from the group consisting of daidzein, genistein, and glycitein, and at least about 5 mg of lycopene, wherein the rate of elevation of PSA is reduced.

11. The method according to claim 10, wherein the effective daily dosage of the composition comprises:
  about 200 IU to about 1200 IU of cholecalciferol;
  about 200 IU to about 1200 IU of D alpha tocopherol;
  about 100 mcg to about 600 µg of selenium;
  about 200 mg to about 1200 mg of epigallocatechin;
  about 160 mg to about 960 mg of saw palmetto berry extract;
  about 10 mg to about 60 mg of daidzein;
  about 10 mg to about 60 mg of genistein;
  about 10 mg to about 60 mg of glycitein; and
  about 5 mg to about 30 mg of lycopene.

12. The method according to claim 10, wherein the composition is administered orally.

13. The method according to claim 10, wherein the composition further comprises one or more of vitamin A, vitamin C, silica, magnesium, maltodextrin, and soy proteins.

14. The method according to claim 10, wherein the composition is administered in combination with chemotherapeutic agents, radiation therapy, or a combination thereof.

15. A method for reducing elevated prostate serum antigen (PSA) levels in a human subject, comprising:
  administering to the human subject a composition comprising in an effective daily dosage at least about 200 International Units (IU) cholecalciferol, at least about 200 IU of D-alpha tocopherol, at least about 100 micrograms (µg) of selenium, at least about 200 milligrams (mg) of epigallocatechin, at least about 160 mg of saw palmetto berry extract, at least about 10 mg of at least one isoflavonoid compound selected from the group consisting of daidzein, genistein, and glycitein, and at least about 5 mg of lycopene, wherein the serum PSA level is reduced.

16. The method according to claim 15, wherein the composition comprises cholecalciferol; D-alpha tocopherol; selenium as L-selenomethionine; epigallocatechin; saw palmetto berry extract; daidzein; genistein; glycitein; and lycopene.

17. The method according to claim 15, wherein the effective daily dosage of the composition comprises:
- at least about 200 International Units (IU) of cholecalciferol;
- at least about 200 IU of D-alpha tocopherol;
- at least about 100 micrograms (µg) of selenium as L-selenomethionine;
- at least about 200 milligrams (mg) of epigallocatechin;
- at least about 160 mg of saw palmetto berry extract;
- at least about 10 mg of daidzein;
- at least about 10 mg of genistein;
- at least about 10 mg of glycitein; and
- at least about 5 mg of lycopene.

18. The method according to claim 15, wherein the effective daily dosage amount of the composition reduces elevated PSA levels in the human subject without decreasing serum testosterone levels.

19. The method according to claim 15, wherein the effective daily dosage is administered as 1 to 3 individual doses.

20. The method according to claim 19, wherein an individual dose comprises about 1 to 8 capsules, tablets, soft gels, or a combination thereof.

* * * * *